(12) United States Patent
Servell et al.

(10) Patent No.: US 9,486,364 B2
(45) Date of Patent: Nov. 8, 2016

(54) DEVICES AND METHODS FOR RESHAPING CARTILAGE STRUCTURES

(71) Applicant: Chondrocyte LLC, Henderson, NV (US)

(72) Inventors: Pascal Servell, Dallas, TX (US); Serge Mordon, Mouvaux (FR); Jack Savage, Sandy, UT (US)

(73) Assignee: Chondrocyte, LLC, Henderson, NV (US)

( * ) Notice: Subject to any disclaimer, the term of this patent is extended or adjusted under 35 U.S.C. 154(b) by 203 days.

(21) Appl. No.: 14/196,963

(22) Filed: Mar. 4, 2014

(65) Prior Publication Data

US 2014/0188158 A1    Jul. 3, 2014

Related U.S. Application Data

(62) Division of application No. 13/498,573, filed as application No. PCT/US2011/000688 on Apr. 15, 2011.

(60) Provisional application No. 61/325,306, filed on Apr. 17, 2010.

(51) Int. Cl.
| | |
|---|---|
| *A61F 2/18* | (2006.01) |
| *A61F 11/00* | (2006.01) |
| *A61B 5/107* | (2006.01) |

(Continued)

(52) U.S. Cl.
CPC ........... *A61F 11/004* (2013.01); *A61B 5/1079* (2013.01); *A61F 2/186* (2013.01); *H04L 29/06* (2013.01); *H04L 67/00* (2013.01); *A61B 2017/00792* (2013.01);

(Continued)

(58) Field of Classification Search
CPC .................... A61B 2017/00787; A61F 11/00; A61F 11/06; A61F 11/004; A61F 2/30756; A61F 5/05891; A61F 5/0102; A61F 2002/183

See application file for complete search history.

(56) References Cited

U.S. PATENT DOCUMENTS

| | | |
|---|---|---|
| 520,785 A | 6/1894 | Jung |
| 1,066,511 A | 7/1913 | Markoff |

(Continued)

FOREIGN PATENT DOCUMENTS

| | | |
|---|---|---|
| CA | 1078690 | 6/1980 |
| JP | 10014971 | 1/1998 |

(Continued)

OTHER PUBLICATIONS

Auri Clinic, website printout, 1 page, http://shop.auriclinic.com/index.php?language=en, visited Oct. 29, 2009.

(Continued)

*Primary Examiner* — Brian Dukert
(74) *Attorney, Agent, or Firm* — Brian C. Trask

(57) ABSTRACT

Described are methods of reshaping a cartilage structure. One such method comprises creating a virtual three dimensional image of the cartilage structure; manipulating the virtual three dimensional image of the cartilage structure so as to obtain a virtual three dimensional image of a desired final shape of the cartilage structure; creating a virtual prototype of a device to hold the cartilage structure in the desired final shape of the cartilage structure; manufacturing the device; lasing the cartilage structure; and fitting the manufactured device to the cartilage structure (e.g., ear).

15 Claims, 5 Drawing Sheets

(51) Int. Cl.
*H04L 29/08* (2006.01)
*H04L 29/06* (2006.01)
*A61B 17/00* (2006.01)

(52) U.S. Cl.
CPC ......... *A61F 2002/183* (2013.01); *H04L 67/42* (2013.01); *H04L 69/329* (2013.01)

(56) References Cited

U.S. PATENT DOCUMENTS

| | | |
|---|---|---|
| 2,339,572 A | 1/1944 | Jurovaty |
| 3,588,914 A | 6/1971 | Ihnat, Jr. |
| 3,889,684 A | 6/1975 | Lebold et al. |
| 4,187,838 A | 2/1980 | Dubrowski |
| 4,670,911 A | 6/1987 | Dunford |
| 4,672,081 A | 6/1987 | Fisher et al. |
| 4,713,843 A | 12/1987 | Duncan |
| 4,850,055 A | 7/1989 | Hwang |
| 4,872,219 A | 10/1989 | Duncan |
| 5,295,950 A | 3/1994 | Godley |
| 5,361,420 A | 11/1994 | Dobbs |
| 5,433,748 A | 7/1995 | Wellisz |
| 5,551,090 A | 9/1996 | Thompson |
| 5,615,417 A | 4/1997 | Jackson |
| 5,673,438 A | 10/1997 | Lambert |
| 5,775,336 A | 7/1998 | Morris |
| 6,093,202 A | 7/2000 | Dyken et al. |
| 6,195,806 B1 | 3/2001 | Campbell |
| 6,517,557 B1 | 2/2003 | Sorribes |
| 6,626,945 B2 | 9/2003 | Simon et al. |
| 6,632,246 B1 | 10/2003 | Simon et al. |
| 6,852,125 B2 | 2/2005 | Simon et al. |
| 6,986,167 B1 | 1/2006 | Coutant et al. |
| 7,025,061 B2 | 4/2006 | Haussmann |
| 7,069,745 B1 | 7/2006 | Finley |
| 7,093,600 B2 | 8/2006 | Sorribes |
| 7,117,546 B2 | 10/2006 | Goulding |
| 7,153,313 B2 | 12/2006 | Whitton |
| 7,335,222 B1 | 2/2008 | Tyler |
| 7,469,429 B1 | 12/2008 | Lanclos |
| 7,850,702 B2 | 12/2010 | Sorribes et al. |
| 8,113,208 B2 | 2/2012 | Chaisson et al. |
| 8,491,510 B2 | 7/2013 | Byrd et al. |
| 8,627,824 B2 | 1/2014 | Koehler |
| 2001/0039455 A1 | 11/2001 | Simon et al. |
| 2004/0039447 A1 | 2/2004 | Simon et al. |
| 2004/0162622 A1 | 8/2004 | Simon et al. |
| 2004/0237175 A1 | 12/2004 | Carrafield |
| 2006/0042640 A1 | 3/2006 | Haussmann |
| 2008/0071255 A1 | 3/2008 | Barthe |
| 2008/0195216 A1 | 8/2008 | Philipp |
| 2008/0269674 A1 | 10/2008 | Stone |
| 2009/0030358 A1 | 1/2009 | Byrd et al. |
| 2010/0204793 A1 | 8/2010 | Byrd et al. |
| 2011/0266265 A1 | 11/2011 | Lang |
| 2012/0185043 A1 | 7/2012 | Byrd et al. |
| 2012/0191005 A1 | 7/2012 | Sobol et al. |
| 2012/0226307 A1 | 9/2012 | Servell et al. |
| 2012/0323227 A1 | 12/2012 | Wolfe |

FOREIGN PATENT DOCUMENTS

| | | |
|---|---|---|
| JP | 4431066 | 3/2010 |
| WO | 0191672 | 12/2001 |
| WO | 2009014908 | 1/2009 |
| WO | 2011/129900 | 10/2011 |
| WO | 2013/142342 | 9/2013 |

OTHER PUBLICATIONS

Earwell TM Infant Ear Correction System, Brochure, Becan Medical Limited, Tucson, Arizona, 2008.
Leclere et al., Laser-Assisted Cartilage Reshaping (LACR) for Treating Ear Protrusions: A Clinical Study in 24 Patients, Aesth Plast Surg. May 30, 2009, published online by Springer.
Mordon et al., Laser Cartilage Reshaping in an In Vivo Rabbit Model Using a 1.54 f.!m Er:Giass Laser, Lasers Surg. Med. 2004, pp. 315-322, vol. 34.
Mordon et al., Correction of ear malformations by Laser Assisted Cartilage reshaping (LACR): a preliminary study in 10 patients, Lasers Surg. Med. 2006, pp. 659-662, vol. 38 No. 7.
PCT International Search Report and Written Opinion, PCT/US2013/032182 dated Jul. 10, 2013.
PCT International Search Report and Written Opinion, PCTUS2011/000688 dated Jan. 17, 2012.
Sorribes, et al., Nonsurgical Treatment of Prominent Ears With the Auri Method, 2002, pp. 1369-1376, vol. 28.
Extended European Search Report and Written Opinion, PCT/US2011000688, P99789EP00, mailed Feb. 26, 2015.
Leclere et al. , Laser-Assisted Cartilage Reshaping for Protruding Ears: A Review of the Clinical Applications, Laryngoscope, 125:2067-2071, 2015.
N. Ignatieva, et al., Molecular processing and structural alterations in laser reshaping of cartilage, Article in Laser Physics letters, Oct. 2007.
Leclere et al. , Cartilage reshaping for protruding ears: A perspective long term follow-up of 32 proceduers, Lasers in Surgery and Medicine 43:875-880 (2011).
Trellos, et al., Correction of ear malformations by laser-assisted cartilage reshaping (LACR), Lasers in Surgery and Medicine 38:659-662 (2006).
Mordon et al., Laser cartilage reshaping in an In Vivo Rabbit model using a 1.54 (micro)m Er:Glass laser, Lasers in Surgery and Medicine 34:315-322 (2004).
Leclere et al. , Laser-Assisted Septal Cartilage Reshaping (LASCR): A prospective study in 12 patients, Lasers in Surgery and Medicine 42:693-698 (2010).

DEVICES AND METHODS FOR RESHAPING CARTILAGE STRUCTURES

CROSS-REFERENCE TO RELATED APPLICATIONS

This application is a divisional of U.S. patent application Ser. No. 13/498,573, filed May 3, 2012, U.S. Pat. No. 8,715,347, which is a national phase entry under 35 U.S.C. §371 of PCT International Patent Application PCT/US2011/000688, filed Apr. 15, 2011, which claims the benefit under 35 U.S.C. §119(e) of U.S. Provisional Application No. 61/325,306 filed Apr. 17, 2010, the contents of the entirety of each of which are incorporated herein by this reference.

TECHNICAL FIELD

The disclosure relates to devices and methods for reshaping cartilage structures, such as a human or mammalian ear.

BACKGROUND

Ear deformations affect 5% of the Caucasian and Latino population or 12.1 million people (5% of 242.3 million). Each year, 4.26 million children are born of white or Latino parents (2.3 million whites and 1 million Hispanics). Of these, approximately 165,000 are born with deformed ears.

However, according to the American Society of Plastic Surgeons (ASPS), only 29,434 cosmetic ear surgery procedures were performed last year in the US and these were primarily performed on children, leaving the vast majority of the population untreated (it is interesting to note that otoplasty is the only cosmetic procedure performed on children, testifying to the damaging psychological issues stemming from this condition).

The average child has 85% ear development by 3 years of age and ears are typically fully grown by the age of 7 years (the height continues to grow into adulthood, but the width and distance from ear to scalp changes little). This fact in part explains why this procedure is popular with children as procedures performed from this age onwards will yield permanent results.

All ears also have surprisingly similar features in terms of size, protrusion from the scalp and angle from the cranium. The following is a list of considered standard sizes: Fully grown ears protrude from the scalp about 1.8-2.0 cm at midpoint. Ear length is typically 5.5-6.5 cm. Ear width is typically 3.0-4.5 cm. The ratio between width and length is about 50% to 60%. Helical Rim (Helix) 7 mm or about 10% of the height. Ear vertical axis 15 to 30 degrees posterior (with the top further back than the bottom).

Features constituting what is considered "normal" ear features are:
Scapha angle greater than 90 degrees. Conchal bowl height less than 1.5 cm. Angle head to ear: female less than 21 degrees; male less than 25 degrees.

Ear deformations typically fall into two broad categories:

Cartilage deformations: these include: Prominent (or "bat") ears which typically is a problem either of an oversized concha, or too wide an antihelical fold angle or a combination of the two. Helical deformations: Constricted ear—hooding or folding of the helical rim; "Lop" ear—the top of the ear is folded down and forward; "Cup" ear—malformed protruding ear with the top folded down and a large concha; Shell ear—curve of the outer rim as well as the folds and creases are missing; and Stahl's ear ("Spock's ear"). There is an extra fold and pointed top.

Non-cartilage related deformations. These include: Lobe deformations, Macrotia (oversized ears), and Microtia (undersized ears).

Surgical Ear Correction: Otoplasty

The first otoplastic technique to correct protruding ears is attributed to Ely in 1881. Since that report, over 180 surgical techniques have been described in the literature for the correction of protruding ears. These techniques can be subdivided into 3 sub-groups:

"Suture only" technique: First described by Furnas in 1968 (and still used to this day), this technique is used primarily to set back the ears and involves retracting the skin behind the ear and place 2-3 non-resorbable sutures to retract the position of the ear. The Mustarde method is today the most common.

Cartilage splitting or weakening technique or "Davis" method: Excision of skin and cartilage to correct conchal hypertrophy.

Combination of the above two or "converse Wood-Smith" technique: uses a cartilage cutting and suture method to correct and create an anti-helical fold.

All these surgical techniques tend to be performed on an outpatient basis under sedation, although when dealing with children it is advisable to perform it under general anesthesia. The procedure is generally performed primarily by Facial Plastic Surgeons and, to a lesser extent by Dermatologists, ENT and Maxillofacial Surgeons. It typically takes 2-3 hours to perform and is not without risks.

Complications from Corrective Ear Surgery:

Major complications can be divided into two categories: Immediate complications: hematoma and infection which may result in necrosis; and Long-term complications include hypertrophic (keloid) scars, loss of sensitivity (resulting from damage to nerve endings), skin and cartilage necrosis as well as unaesthetic results or recurrence of the ear deformity. It is important to realize that these complications are responsible for the high (10%) rate of repeat surgeries.

BRIEF SUMMARY OF THE DISCLOSURE

Embodiments include a device for reshaping cartilage structures, the device comprising a first portion (also referred to herein as a trellis or ear trellis) fitting over the helix of the outer ear, and a second portion (also referred to herein as a "projection") having a proximal end and a distal end, the proximal end of the second potion projecting from and attached to the first portion; wherein, when the device is fitted to an ear, the second portion extends from the first portion, across the anti-helix and the distal end of the second portion fits into the scapha under the helix at about the lower crura of the anti-helix and/or the fossa trangularis.

In certain embodiments, the device (trellis) is designed so as to fit between the head and the rear surface of the ear. Certain embodiments of the device comprise a first surface configured to fit against and be attached to the head behind the ear, a second surface configured to fit against and be attached to the rear surface of the ear so as to hold the ear in a desired position, and connecting structure configured so as to hold the first surface and the second surface in position relative to one another.

Disclosed is a method of reshaping a cartilage structure, the method comprising: creating a virtual three dimensional image of the cartilage structure; manipulating the virtual three dimensional image of the cartilage structure so as to obtain a virtual three dimensional image of a desired final shape of the cartilage structure; creating a virtual prototype of a device to hold the cartilage structure in the desired final shape of the cartilage structure; manufacturing the device; lasing the cartilage structure; and fitting the manufactured device to the cartilage structure. In certain embodiments, fitting the manufactured device to the cartilage structure includes attaching the manufactured device to the cartilage structure and also may include attaching the device to a non-cartilage structure (e.g., the head).

Disclosed is a method of shaping or reshaping a cartilage structure, the method comprising: creating a virtual three dimensional image of the location or cavity to contain the cartilage structure; manipulating the virtual three dimensional image of the location or cavity to contain the cartilage structure so as to obtain a virtual three dimensional image of a desired final shape of the cartilage structure; creating a virtual prototype of a device with an inner surface conforming to the desired final shape of the cartilage structure; manufacturing the device; lasing the cartilage structure; placing the cartilage in the device and placing the device in culture medium; growing the cartilage to conform to the inner surface of the device; and placing the grown cartilage into the location or cavity.

Also disclosed is a method of shaping a subject's ear comprising analyzing the ear and determining what the desired shape of the ear is, manufacturing an encasing structure or trellis that includes an inner portion or cavity that is of the desired shape, lasing the ear, encasing at least a portion of the lased ear within the encasing structure so that the lased ear is formed into the desired shape, and allowing the ear thus to form. Structures capable of encasing the ear are known in the art. See, e.g. U.S. Pat. App. Pub. 2009/0030358, the entirety of the contents of which is incorporated herein by reference.

The methods and means described herein are much more effective, of broader applicability (e.g., can be applied to subjects such as a human or mammal), less painful, and less expensive than the prior art methodology.

DETAILED DESCRIPTION

Figure 4:
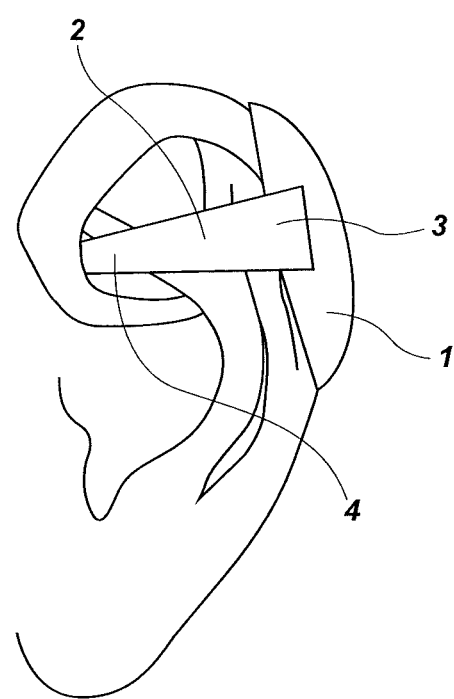
FIG. 4 is a depiction of one embodiment of a device described herein.

Certain embodiments include a device (a trellis) for reshaping cartilage structures. With reference to FIG. 4, of the depicted device comprises an ear trellis (1), fitting over the helix of the outer ear, and a projection (2), originating and attached to the ear trellis (1) at its proximal end (3), and extending across the anti-helix and the distal end (4) fitting into the scapha under the helix at about the lower crura of the anti-helix and/or the fossa trangularis. The projection (2) and ear trellis (1) may be formed as a single piece or as multiple pieces.

In certain embodiments, the projection (2) may be of a length or have a bias such that when fitted into an ear, the projection (2) exerts pressure on its distal end (4) and proximal end (3) so as to force the ear trellis away from the distal end (4) and towards the mastoid. In certain embodiments, the length or the bias of the projection (2) is adjustable such that greater or lesser pressure is exerted by the distal end (4) on the ear and/or by the proximal end (3) on the ear trellis. In certain embodiments, the projection (2) is formed of any suitable material including plastic or metal. In particular embodiments, the projection (2) if formed from a material that is capable of being biased to return to a particular shape such that when the projection (2) is deflected from its biased shape, it exerts pressure to return to its undeflected shape.

In certain embodiments, the length of the projection (2) is adjustable. For example the projection (2) may be constructed of one or more pieces that may lock together in one or more configurations to provide different lengths of the overall projection (2). By way of non-limiting example, a first portion (1) of the projection (2) may have one or more holes or depressions and a second portion of the projection (2) may have one or more pins or studs such that the two portions may be fit together to form projections of various lengths. In another non-limiting example, the length of the projection (2) may be adjustable in where along the length of the projection (2) it attaches to the ear trellis, thus providing various lengths of projection (2) that extend from the ear trellis to the distal end (4).

In further embodiments, the attachment of the proximal end (3) of the projection (2) to the ear trellis is adjustable such that the proximal end (3) may be attached to the ear trellis at different and/or multiple locations. By way of non-limiting example, the ear trellis may have multiple attachment points for the projection (2) along its length such that the point of attachment of the projection (2) to the ear trellis is adjustable along the length of the helix to which the ear trellis may be attached.

In certain embodiments, the distal end (4) of the projection (2) is molded for comfortable fit in the scapha or may be covered with another material so as to provide additional comfort to the user.

In certain embodiments, the ear trellis (1) may attach to all or part of the helix. In a particular embodiment, the ear trellis fits around the helix with at least a portion of the ear trellis extending into the scapha. In certain embodiments, the ear trellis grips the helix such that when pressure is applied to the ear trellis from the proximal end (3) of the projection (2), it remains attached to the helix and forces the helix toward the mastoid. In certain embodiments, the ear trellis (1) may be configured to be attached and/or may be attached to the mastoid or the skin covering the mastoid.

In certain embodiments, the ear trellis may extend further behind or in front of the ear so as to contact and place pressure upon structures other than the helix and/or the scapha. By way of non-liming example, the ear trellis might extend to and place pressure upon one or more of the helix, scapha, fossa triagularis, either of the crura of the antihelix, scaphoid fossa, crus of the helix, tragus, antitragus, cybma conchae, and cavum conchae. In certain examples, the ear trellis may place pressure on any one or more of the aforementioned structures so as to hold it in a desired position.

In particular embodiments, the trellis to be applied (which need not be affixed to the subject's head) flattens a hyper-curved ear by sandwiching the misshapen ear between a first member and a second member that extend along both the inside and outside of the upper portion of the ear or encase the entire upper portion of the ear so that, after laser application, the ear may be formed to more approximate a desired shape. The first and second members, e.g., in the case when the trellis encases the upper portion of the ear (not shown), may be integrally formed, or may alternatively be two distinct flat, longitudinal members affixed to one another, via, e.g., a hinge, clip, or springed hinge, that act to flatten the ear between the flat longitudinal members or projections. In such a case, the device depicted in FIG. 4 has a second projection (not shown) running generally parallel to the projection, but extending behind the ear to sandwich the ear. Once sized and placed on the subject's ear, the two generally parallel projections act to flatten the upper portion of the ear extending between them thus flattening the hyper-curved portion after laser treatment.

Figure 5:
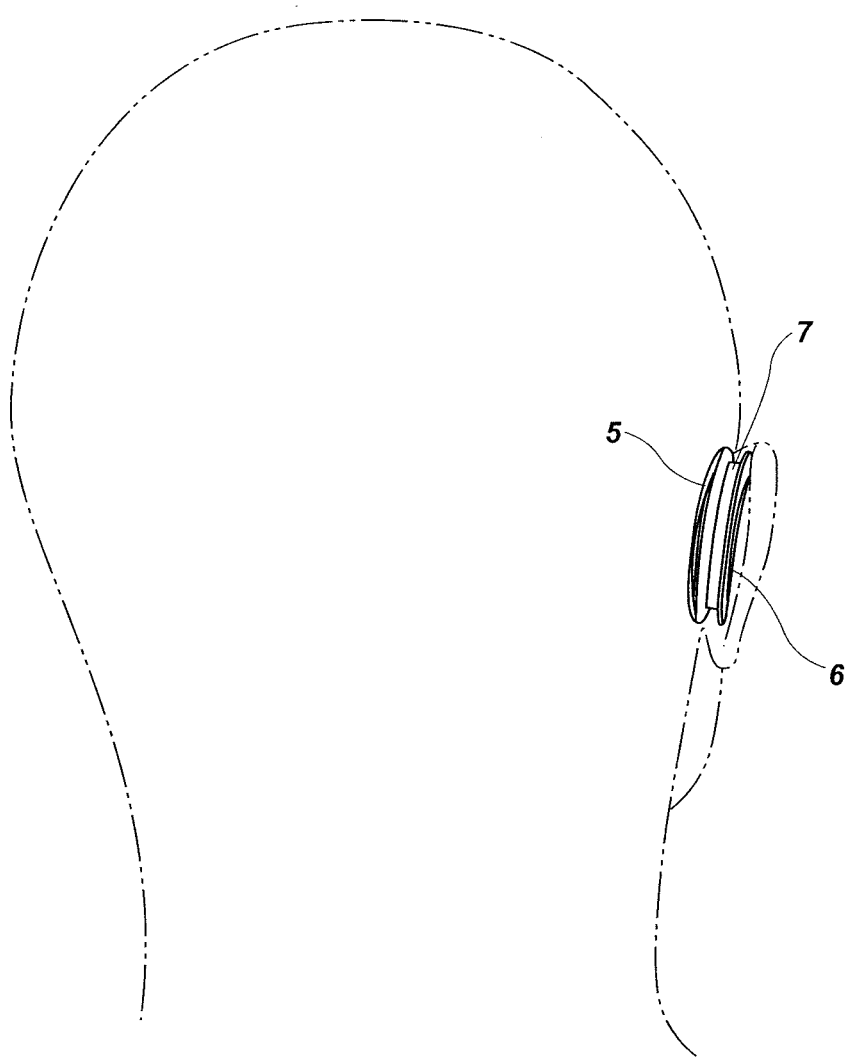
FIG. 5 is a depiction of a further embodiment of a device described herein.

In certain embodiments, the device (trellis) is designed so as to fit between the head and the rear surface of the ear. With reference to FIG. 5, certain embodiments of the device comprise a first surface (5) configured to fit against and be attached to the head behind the ear, a second surface (6) configured to fit against and be attached to the rear surface of the ear so as to hold the ear in a desired position, and connecting structure (7) configured so as to be attached the first surface (5) and the second surface (6) so as to the hold the first surface (5) and the second surface (6) in position relative to one another. In certain embodiments, the first surface (5), second surface (6), and connecting structure (7) may be formed as a single piece or multiple pieces.

In certain embodiments, the first surface (5) may be molded, sculpted, or manufactured so as to fit comfortably against the skin on the head behind the ear. In certain embodiments, the second surface (6) is molded, sculpted, or manufactured so as to provide a surface conforming to a final desired position and shape of the ear. In embodiments, the first surface (5) and the second surface (6) may be fixed in place relative to one another by connecting structure (7) such that when first surface (5) is attached to the skull, or the skin over the skull (e.g., the head behind the ear), and second surface (6) is attached to the rear of the ear, the ear is held in a desired position and/or configuration.

In certain embodiments, the first surface (5) and the second surface (6) may be attached to the skin, skull, or ear in any permanent, semi-permanent, or non-permanent way as desired. Examples of articles or items useful in attaching the device include, but are not limited to, screws, clips, wires, staples, nails, brads, adhesives, tapes, sutures, cements, and glues.

In further embodiments, the attachment of the first surface (5) and the second surface (6) to the connecting structure (7) may be adjustable such that first surface (5) and the second surface (6) may be attached to the connecting structure (7) at different and/or multiple locations or configurations. By way of non-limiting example, the connecting structure (7) may have multiple attachment points for first surface (5) and the second surface (6) along its length such that the point of attachment of the first surface (5) and the second surface (6) to the connecting structure (7) is adjustable.

In certain embodiments, the second surface (6) may attach to all or part of the rear surface of the ear. In a particular embodiment, the second surface (6) fits around the helix with at least a portion of the second surface (6) extending into the scapha. In certain embodiments, the second surface (6) grips the helix such that when the first surface (5) is attached to the skull, or the skin over the skull, behind the ear, the second surface (6) forces the helix toward the mastoid.

In certain embodiments, the second surface (6) may extend further behind or in front of the ear so as to contact and place pressure upon structures other then the helix and/or the scapha when the first surface (5) is attached to the skull, or the skin over the skull, behind the ear. By way of non-liming example, the second surface (6) might extend to and place pressure upon one or more of the helix, scapha, fossa triagularis, either of the crura of the antihelix, scaphoid fossa, crus of the helix, tragus, antitragus, cybma conchae, and cavum conchae. In examples, the second surface (6) may place pressure on any one or more of the aforementioned structures so as to hold it in a desired position.

Certain embodiments of the trellis structures may fit in and/or around the nose. In certain embodiments, a trellis includes one or more portions that extend into one or more of the nasal cavities. In certain embodiments, a trellis may also contain one or more portions that extend over the one more of the outer surfaces of the nose or the face. In certain embodiments, potions of the trellis that extend into the nasal cavities may be tubular or hollow in nature so as to allow the passage of air through the trellis and into the upper nasal cavities.

Certain embodiments of the disclosure include trellis structures that close completely or partially around the cartilage structure. For example, the cartilage structure may comprise a whole, or portion of a spinal disc or meniscus of the knee for which the trellis would completely or partially enclose. In certain embodiments, the trellis may have holes in it or be made of a porous material to allow the passage of liquids and/or small molecules through the surface of the trellis.

In certain embodiments, a trellis is constructed of any rigid or semi-rigid material such as metal or plastic. In certain embodiments, the trellis is constructed of one or more pieces such as a back piece (to cover, for example, a portion of the rear surface of the ear or the interior portion of the nasal cavity) and a front piece (to cover, for example, a portion of the front surface of the ear and/or fit in to the scapha or an exterior potion of the nose). The first and second pieces may be joined in any suitable manner such as permanently joining (for example fusing or welding) or non-permanently joining (for example held to together by one or more of pins, clips, hinges, locking mechanisms, etc.). In certain embodiments, the trellis is designed so as to be easily removable from the underlying cartilage structure.

Certain embodiments of the disclosure include methods of forming or reforming cartilage structures in a subject using the devices described herein. The forming or reforming of cartilage structures may take place through the process of chondrogensesis. In certain embodiments, the cartilage structures may be any cartilage containing portion of a subject including, but not limited to, the joints between bones, the rib cage, the ear, the nose, the elbow, the knee, the ankle, the bronchial tubes, the intervertebral discs, and nasal septum. One example of such a method comprises treating a cartilage structure with a laser so as to stimulate chonrdogenesis as described by Leclere et al. (Aesth. Plast. Surg. 2010 April; 34(2):141-6); Mordon et al. (Lasers Surg. Med. 2004 34:315-322) and Mordon et al. (Lasers Surg. Med. 2006 August; 38(7):659-62) the contents of the entirety of each of which are incorporated herein by reference.

In certain embodiments, the laser used to treat the cartilage structure may be a mid IR laser. In further embodiments, the laser may emit radiation at a wavelength of about 1540 nm. In certain embodiments, the laser may be 1540 nm Er:YAG laser such as that available from Quantel Derma GmbH, Erlangen Germany. In additional embodiments, the tip of the laser may incorporate an integrated cooling device such that, when in use, the cooled tip of the device imparts a cooling effect on any tissue or cartilage structure being irradiated by the laser. One non-limiting example of such a cooling tip is the Koolburst, available from Quantel Derma GmbH, Erlangen Germany utilizing the manufacturer's instructions.

In certain embodiments, lasing of the cartilage structure may deliver about 84 J/cm$^2$ cumulative fluence. In certain embodiments, the cumulative fluence may be delivered in a single pulse or by the stacking of several pulses. By way of a non-limiting example, 84 J/cm$^2$ cumulative fluence may be achieved by delivering seven stacked pulses of 12 J/cm$^2$.

In certain embodiments, lasing of the cartilage structure may comprise lasing of one or more of the surfaces of the cartilage structure. By way of non-limiting examples, lasing of the ear may comprise lasing of both sides of the ear at the location to be stimulated, for example both sides of the entire helix and concha of the ear; lasing of the nasal septum may comprise lasing both surfaces of the septum; and lasing a spinal disc or meniscus of the knee may comprise lasing all or some of the surfaces of these structures. In further embodiments, locations of a cartilage structure to be lased may include the entire structure or may be limited to particular portions of a cartilage structure in order to achieve a desired localization of chonrdogenesis.

In certain embodiments, the above described trellis or similar devices is placed on the cartilage structure and left in place until the cartilage structure is effectively reshaped by the trellis or similar device. In certain embodiments, the trellis or similar device is left in place for a period of 3 to 6 weeks. In particular embodiments, the trellis is worn continuously for the first 3 weeks and then only at night for an additional 3 weeks.

In certain embodiments, the trellis is specifically designed to hold the cartilage structure in a desired shape or grow the structure into a desired shape. In certain embodiments, the cartilage structure to be treated and/or lased is scanned or imaged in three dimensions so as to create a virtual or electronic version of the cartilage structure. Devices for creating three dimensional virtual images of objects are known in the art and include, but are not limited to MRI, PET, CT, and 3D scanners (hand held or otherwise) such as, but not limited to the hand held Handyscan™ 3D scanners available from Creafrom, Quebec City, Quebec, Canada utilizing the manufacturer's instructions. In certain embodiments, a three dimensional image of the cartilage structure to be shaped is manipulated using various commercially available software programs so such the final desired form of the cartilage structure is rendered. One example of such software includes, but is not limited to, Mimics Z software available from Z Corp, Burlington, Mass.

In certain embodiments, the cavity or locale which wholly or partially contains the cartilage structure is scanned so as to create a three dimensional virtual model of the location into which the cartilage structure is desired to fit and/or function. Once a virtual model of the cavity or locale is rendered, the shape of the virtual cavity or locale may be manipulated using various commercially available software programs so that the final desired form of the cartilage structure is rendered.

Once the final desired form of the cartilage structure is rendered, a virtual prototype trellis according to the disclosure is designed to fit and hold the cartilage structure in a desired position or dimension. An actual device from the virtual prototype trellis may then be manufactured using techniques available in the art. In one non-limiting example, the trellis may be manufactured from the virtual prototype trellis using a 3D printer such as the ones available from Z Corp, Burlington, Mass. utilizing the manufacturer's instructions.

Figure 1:
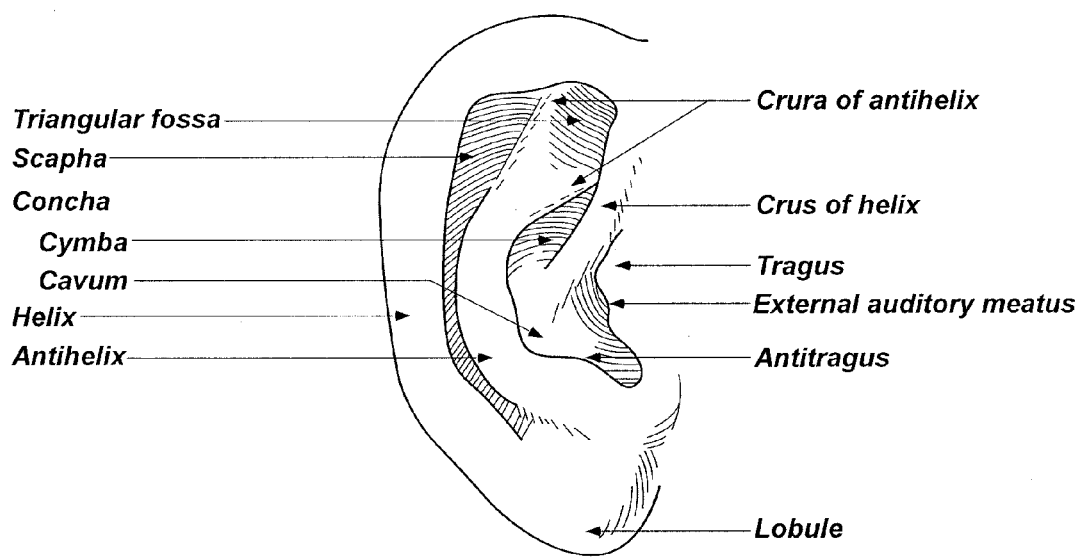
FIG. 1 is a depiction of the structures of the outer ear.
Figure 2:
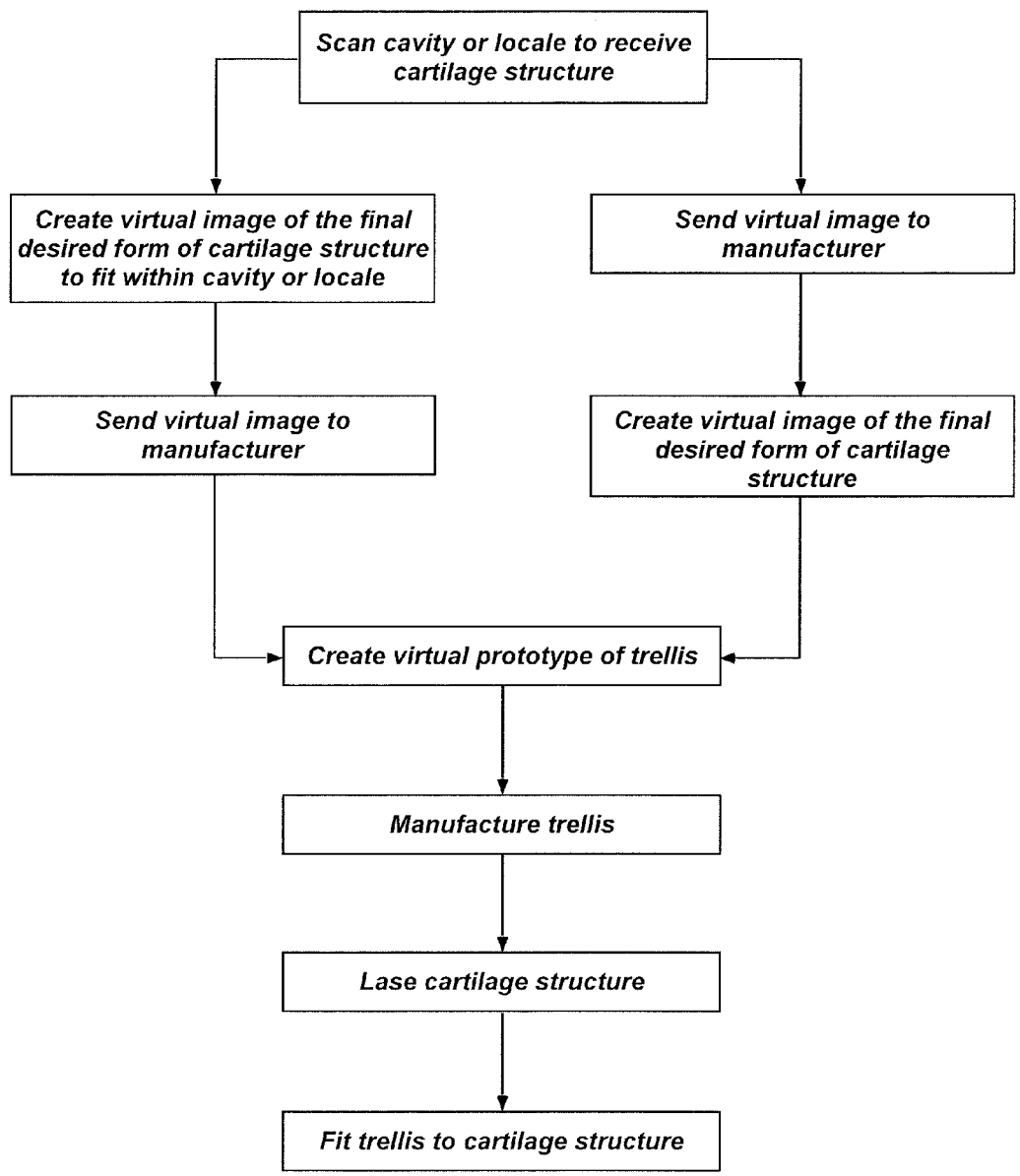
FIG. 2 is a flow chart of one embodiment of a method described herein.

In one embodiment, as depicted in the flow chart presented in FIG. 2, a subject may visit a provider to have the cartilage structure, or a cavity or locale containing a cartilage structure, scanned. A copy of the scan may then be sent to a manufacturer. The sending of the scan may be done in any practical way such as, but not limited to, physically or through electronic means such a memory device or the internet. Either the provider or the manufacturer may manipulate the virtual image created by the scan to produce a virtual image of the final desired form of the cartilage structure. The manufacturer may then create a virtual prototype trellis designed to hold the cartilage structure in the desired position or define the final shape of the cartilage structure. The manufacturer may then manufacture the trellis and provide the completed trellis to the provider. The provider or some other entity may lease the cartilage structure as herein described and then the cartilage structure may then be fitted with the trellis. The trellis may then be worn by the subject until the cartilage structure assumes the desired final form.

Figure 3:
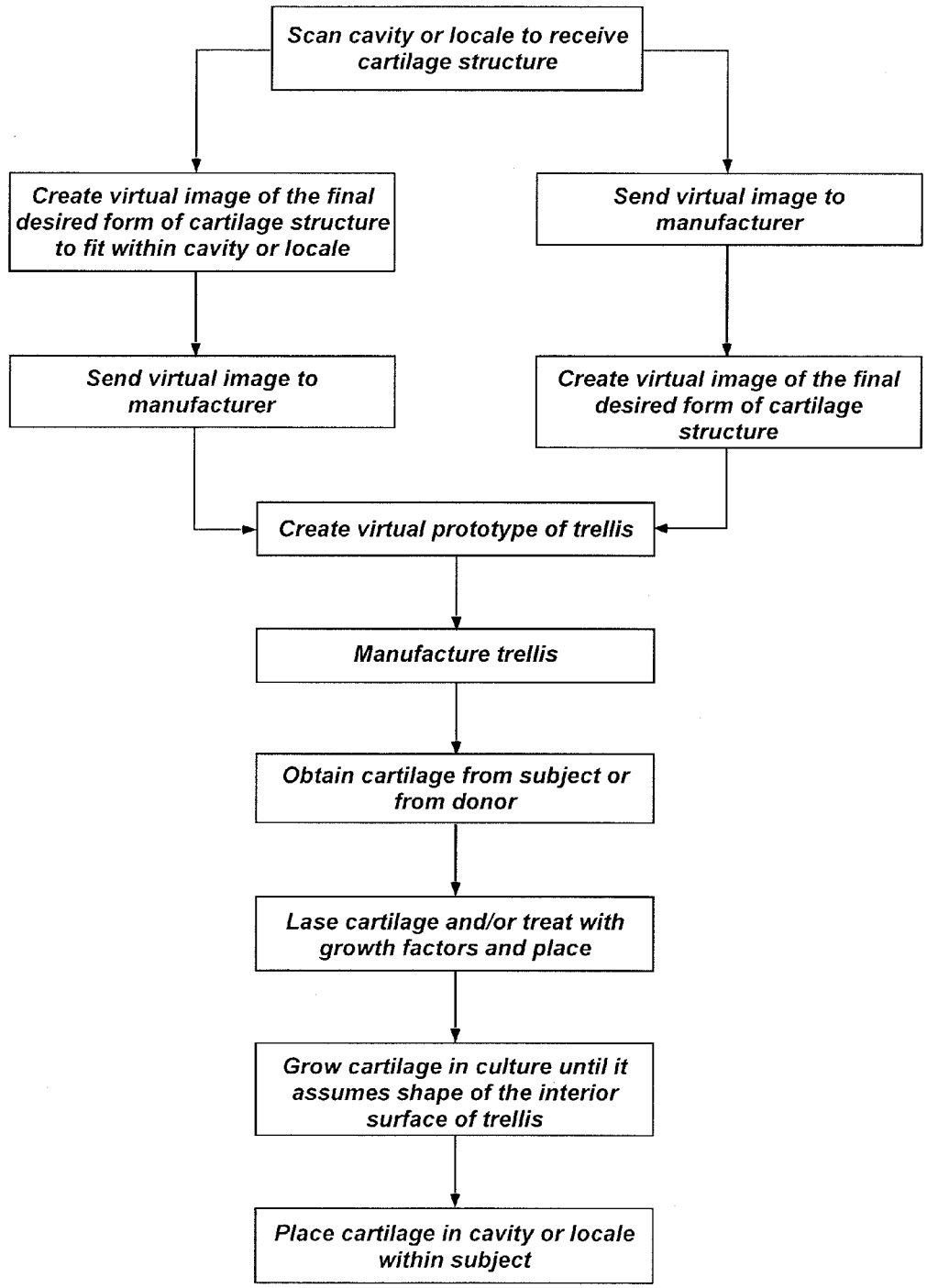
FIG. 3 is a flow chart of one embodiment of a method described herein.

In certain embodiments, a trellis may be created to define the final shape for a cartilage structure to be inserted into a particular cavity or locale within a subject. As depicted in the flow chart presented in FIG. 3, a three dimensional virtual image of the cavity or locale may be created as described herein. A three dimensional virtual image of the cartilage structure to be placed in the cavity or locale may then be designed and manufactured to help define the outer limits of the cartilage structure. Cartilage from a subject or a donor may then be obtained and placed into culture within the manufactured trellis. The cartilage in culture may be lased as described herein and/or exposed to various factors known to effect the growth and maturation of cartilage such as, but not limited to, IGF-I, TGF-beta1, BMP-7, PDGF-AB; and FGF-2. Once the cartilage has assumed the desired shape, it may be removed from culture and placed into the cavity or locale in the subject.

The application includes the following example, which is offered by way of illustration and not intended to limit the invention in any manner.

Example 1

Laser-Assisted Cartilage Reshaping for Treating Ear Protrusions

Materials and Methods

Twenty-four patients were treated by LACR. All patients were informed of the purpose and possible outcomes of the study, signed forms of consent for the study, and agreed to clinical photography. There were 14 adults and 10 children. The patients' mean age was 16.0 years (range=6-45 years). Pain was assessed by the patients using a 4-point scale: none, slight, moderate, or severe.

For 21 patients, the 1.54-ImEr:YAG laser (Aramis, Quantel Derma GmbH, Erlangen, Germany) was set at 12 J/cm2 per pulse. The treatment consisted of seven stacked pulses (3 ms, 2 Hz, 84 J/cm2 cumulative fluence) applied using a 4-mm spot hand piece with integrated cooling (Koolburst, Quantel Derma GmbH, Erlangen, Germany) on both sides of the entire helix and concha. For the remaining three adults, the laser was set at a lower fluence of 10 J/cm2 per pulse for a total cumulative fluence of 70 J/cm2. The entire helix and concha were irradiated on both sides. Contact cooling made the treatment very tolerable, to the extent that topical anesthesia was not required (although local anesthetic certainly could have been used).

Twenty-four patients underwent LACR of both ears using our 1.54-lm laser. Immediately after irradiation, a silicone elastomer (Hydro-C, Detax, Ettlingen, Germany) was inserted inside the helix to give it the desired shape. Three minutes later the elastomer hardened and a solid mold was obtained. The entire procedure took no more than 15-20 min per ear. Patients were asked to wear this mold at all times for the first 3 weeks and then only at night for an additional 3 weeks. A non-steroidal anti-inflammatory drug (NSAID) was prescribed to all patients for 3 days. Ears were checked at days 1, 30, 60, and 90 and photographs were taken. Clinical follow-up at 1 year was obtained via direct patient contact (n=22) or over the telephone (n=2).

Results

Postoperative follow-up was uneventful for all ears, except for six on which minor contact dermatitis developed probably because of inappropriate mold design. This did not require additional therapy and those patients (4 children and 2 adults) stopped wearing the mold leading to incomplete shape correction. There were no cases of infection hematomas or skin necrosis. For the remaining 18 patients (6 children and 9 adults) the expected ear reshaping was achieved (fluence=84 J/cm2) Table 1; in 3 adults, partial or incomplete reshaping was observed and correlated to a lower fluence (70 J/cm2). Those patients were retreated at months at 84-J/cm2 fluence and all achieved suitable reshaping (Table 2). Again, no postoperative discomfort was reported.

TABLE 1

Our series of 48 reshaped ears using the 1540-nm laser on 24 patients

| N | Age (years) | Sex | Fluence (J/cm$^2$) | Mold | Reshaping | Pain | Follow-up (months) |
|---|---|---|---|---|---|---|---|
| 1 | 6 | M | 84/84 | A/A | E/E | N/N | St/St |
| 2 | 6 | M | 84/84 | A/A | E/E | N/N | St/St |
| 3 | 7 | W | 84/84 | A/A | E/E | N/N | St/St |
| 4 | 7 | W | 84/84 | A/A | E/E | N/N | St/St |
| 5 | 6 | W | 84/84 | A/A | E/E | N/N | St/St |
| 6 | 8 | W | 84/84 | A/A | E/E | N/N | St/St |
| 7 | 19 | W | 84/84 | A/A | E/E | N/N | St/St |
| 8 | 24 | W | 84/84 | A/A | E/E | N/N | St/St |
| 9 | 22 | W | 84/84 | A/A | E/E | N/N | St/St |
| 10 | 20 | W | 84/84 | A/A | E/E | N/N | St/St |
| 11 | 16 | W | 84/84 | A/A | E/E | N/N | St/St |
| 12 | 18 | M | 84/84 | A/A | E/E | N/N | St/St |
| 13 | 22 | M | 84/84 | A/A | E/E | N/N | St/St |
| 14 | 22 | W | 84/84 | A/A | E/E | N/N | St/St |
| 15 | 45 | W | 84/84 | A/A | E/E | N/N | St/St |
| 16 | 24 | W | 84/84 | I/I | I/I | N/N | MR/MR |
| 17 | 22 | W | 84/84 | I/I | I/I | N/N | MR/MR |
| 18 | 8 | W | 84/84 | I/I | I/I | N/N | MR/MR |
| 19 | 6 | W | 84/84 | I/I | I/I | N/N | MR/MR |
| 20 | 6 | W | 84/84 | I/I | I/I | N/N | MR/MR |
| 21 | 8 | M | 84/84 | I/I | I/I | N/N | MR/MR |
| 22 | 22 | M | 70/70 | A/A | I/I | N/N | SeR/SeR |
| 23 | 18 | W | 70/70 | A/A | I/I | N/N | SeR/SeR |
| 24 | 22 | W | 70/70 | A/A | I/I | N/N | SeR/SeR |

M man,
W woman,
R/L right/left,
A appropriate,
I inappropriate,
E expected,
I incomplete,
N none,
S slight,
M moderate,
Se severe,
St stable,
SR slight recurrence,
MR moderate recurrence,
SeR severe recurrence

TABLE 2

Three patients underwent a second course of reshaping with a new fluence

| N | Age (years) | Sex | Fluence (J/cm$^2$) | Mold | Reshaping | Pain | Follow-up (months) |
|---|---|---|---|---|---|---|---|
| 22 | 22 | M | 84/84 | A/A | E/E | N/N | St/St |
| 23 | 18 | W | 84/84 | A/A | E/E | N/N | St/St |
| 24 | 22 | W | 84/84 | A/A | E/E | N/N | St/St |

M male,
W woman,
A appropriate,
E expected,
N none,
St stable

What is claimed is:

1. A method of shaping a subject's ear to a desired shape and/or position, the method comprising:
    analyzing the subject's ear to determine what the ear's desired shape and/or position is,
    providing an ear trellis that comprises an encasing structure for the ear that includes an inner portion that corresponds to a portion of the ear's desired shape,
    lasing the ear so as to stimulate chondrogenesis in the ear,
    encasing at least a portion of the lased ear within the encasing structure so that the lased ear is able to form into the desired shape and/or position, and
    maintaining the ear within the encasing structure thus to form the lased ear into the desired shape and/or position.

2. The method according to claim 1, wherein the encasing structure is maintained on the subject's ear for a period of at least three weeks.

3. The method according to claim 1, wherein the ear trellis comprises:
    a first portion fitting over the helix of the subject's outer ear, and
    a second portion having a proximal end and a distal end, the proximal end projecting from and attached to the first portion;
    wherein, when the device is associated with the subject's ear, the second portion extends from the first portion, across the ear's anti-helix, and the distal end of the second portion fits into the ear's scapha under the helix at about the lower crura of the anti-helix and/or the fossa trangularis; and
    wherein the first portion comprises a first surface configured to fit against and be attached to the skull, or the skin over the skull, behind the ear.

4. The method according to claim 3, wherein the second portion is of a length or has a bias such that when associated with the subject's ear, the second portion exerts pressure on its distal and proximal ends so as to force the first portion and the helix away from the distal end and towards the mastoid.

5. The method according to claim 3, wherein the first portion has a single potential attachment point for the second portion.

6. The method according to claim 3, wherein the first portion further comprises a projection that extends around the ear's helix and fits into the scapha.

7. The method according to claim 1, wherein the ear trellis comprises:
    a first surface configured to fit against and be adhered to the subject's head behind the ear, and, upon fitting of the device onto the subject, hold the ear in a relative position with respect to the head; and a second surface configured to fit against and be attached to the rear surface of the ear, wherein the second surface provides a shaping surface conforming to the ear's desired final shape.

8. The method according to claim 1, wherein:

the encasing step comprises affixing a first portion of the ear trellis to the subject's head.

9. The method according to claim 8, wherein:

the ear trellis is installed to dispose a portion of the trellis at a position between the rear surface of the ear and the skull.

10. The method according to claim 8, wherein:

the affixing step is accomplished by way of an adhesive bond between the subject's skin and the first portion.

11. The method according to claim 8, further comprising:

positioning a projection of the ear trellis to extend across the helix and contact the front surface of the ear, the projection then having a bias effective to urge the ear toward a desired shape and/or position.

12. The method according to claim 11, wherein:

a distal end of the projection is positioned in the ear's scapha under the helix at about the lower crura of the anti-helix and/or the fossa trangularis.

13. The method according to claim 9, further comprising:

attaching a second portion of the ear trellis to the rear surface of the ear effective to urge the ear toward a desired shape and/or position.

14. The method according to claim 13, wherein:

attaching the second portion of the ear trellis to the rear surface of the ear causes the trellis to apply tension to a portion of the rear surface of the ear effective to urge the ear toward a desired shape and/or position.

15. The method according to claim 1, wherein:

the encasing step comprises disposing the ear trellis to sandwich the ear such that a first portion of the ear trellis is in contact with a portion of the rear surface of the ear and a second portion of the ear trellis is in contact with a portion of the front surface of the ear.

* * * * *